United States Patent [19]

Siedlecki, Jr. et al.

[11] Patent Number: 4,799,376
[45] Date of Patent: Jan. 24, 1989

[54] CLOUD WATER MEASUREMENT

[75] Inventors: Walter F. Siedlecki, Jr., West Chester; Kenneth R. Horst, Cincinnati, both of Ohio

[73] Assignee: General Electric Company, Cincinnati, Ohio

[21] Appl. No.: 813,359

[22] Filed: Dec. 26, 1985

[51] Int. Cl.$^4$ ............................................. G01N 31/00
[52] U.S. Cl. .......................................... 73/29; 73/335; 73/863.03; 73/863.11
[58] Field of Search .................. 73/29, 863.02, 863.03, 73/863.11, 863.12, 61.1 R, 335, 336.5

[56] References Cited

U.S. PATENT DOCUMENTS

| | | | |
|---|---|---|---|
| 2,541,512 | 2/1951 | Hahn | 244/134 |
| 2,755,456 | 7/1956 | Bursack | 340/234 |
| 2,814,948 | 12/1957 | Neel, Jr. | 73/170 |
| 3,252,323 | 5/1966 | Torgeson | 73/170 |
| 3,498,108 | 3/1970 | Ruskin et al. | 73/29 |
| 3,842,678 | 10/1974 | De Baum et al. | 73/863.03 |
| 4,091,835 | 5/1978 | Frampton | 73/863.03 |
| 4,222,261 | 9/1980 | Leblance | 73/29 |
| 4,356,834 | 11/1982 | Le May | 73/2.9 |

FOREIGN PATENT DOCUMENTS 3024 1/1982 Japan ........................ 73/29

Primary Examiner—Stewart J. Levy
Assistant Examiner—Hezron E. Williams
Attorney, Agent, or Firm—Derek P. Lawrence; Nathan D. Herkamp

[57] ABSTRACT

An incoming airstream is channeled into a diffuser to reduce its spread. Heating coils heat the air in order to vaporize any water present. Then, a collection pipe draws off a portion of vaporized mixture and transmits it to a dew point meter at which the water content is ascertained. The remaining mixture bypasses the collection pipe and is expelled.

4 Claims, 2 Drawing Sheets

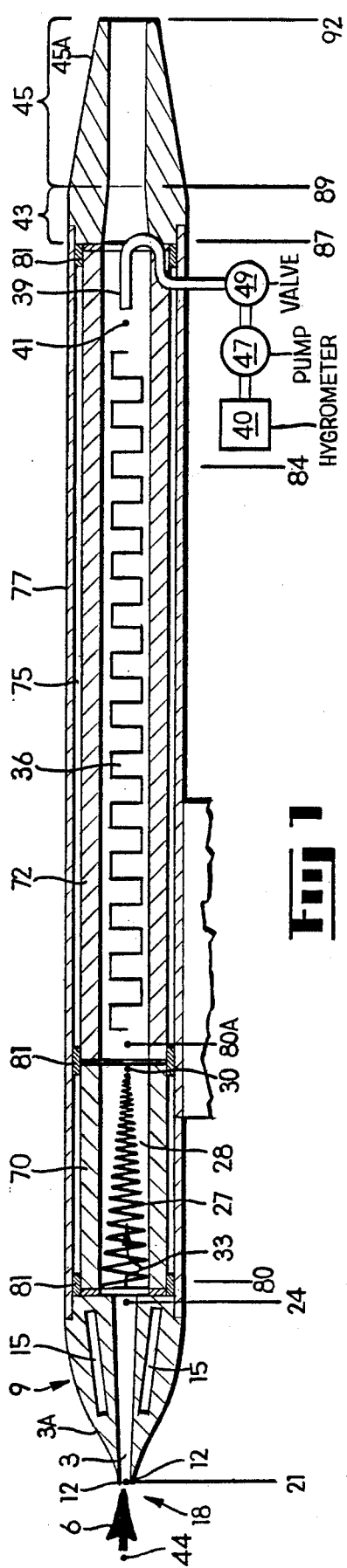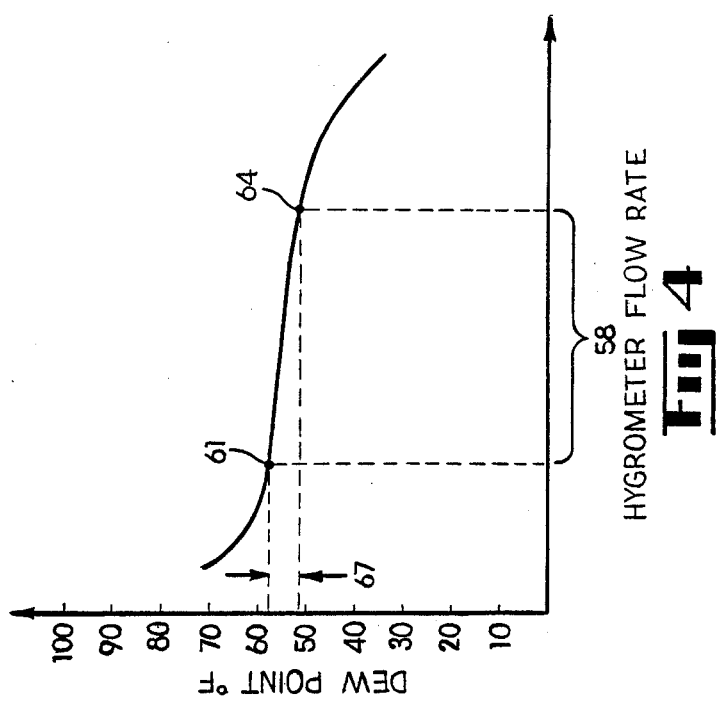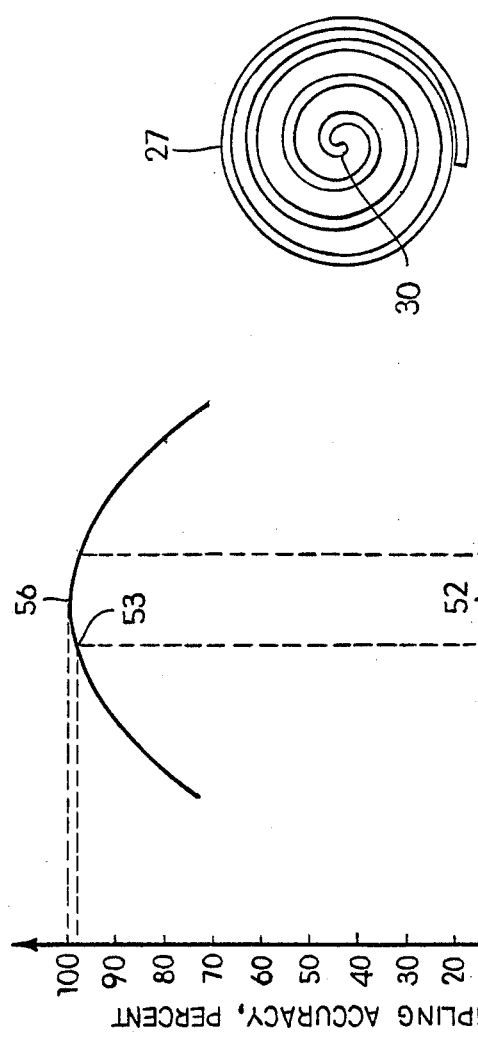

CLOUD WATER MEASUREMENT

OBJECTS OF THE INVENTION

It is an object of the present invention to provide new and improved measurement of the water content of a moving airstream, especially when the water is not in the vapor state.

SUMMARY OF THE INVENTION

In one form of the invention, an incoming airstream is channeled into a diffuser to reduce its speed. Heating coils heat the air in order to vaporize any water present. Then, a collection pipe draws off a portion of vaporized mixture and transmits it to a dew point meter at which the water content is ascertained. The remaining mixture bypasses the collection pipe and is expelled.

BRIEF DESCRIPTION OF THE DRAWINGS

FIG. 1 depicts one form of the invention.
FIG. 2 is an end-on view of the coil 27 in FIG. 1.
FIGS. 3 and 4 are graphs of expected performance of the invention which are used to establish isokinetic operation.

DETAILED DESCRIPTION OF THE INVENTION

Figure 5:
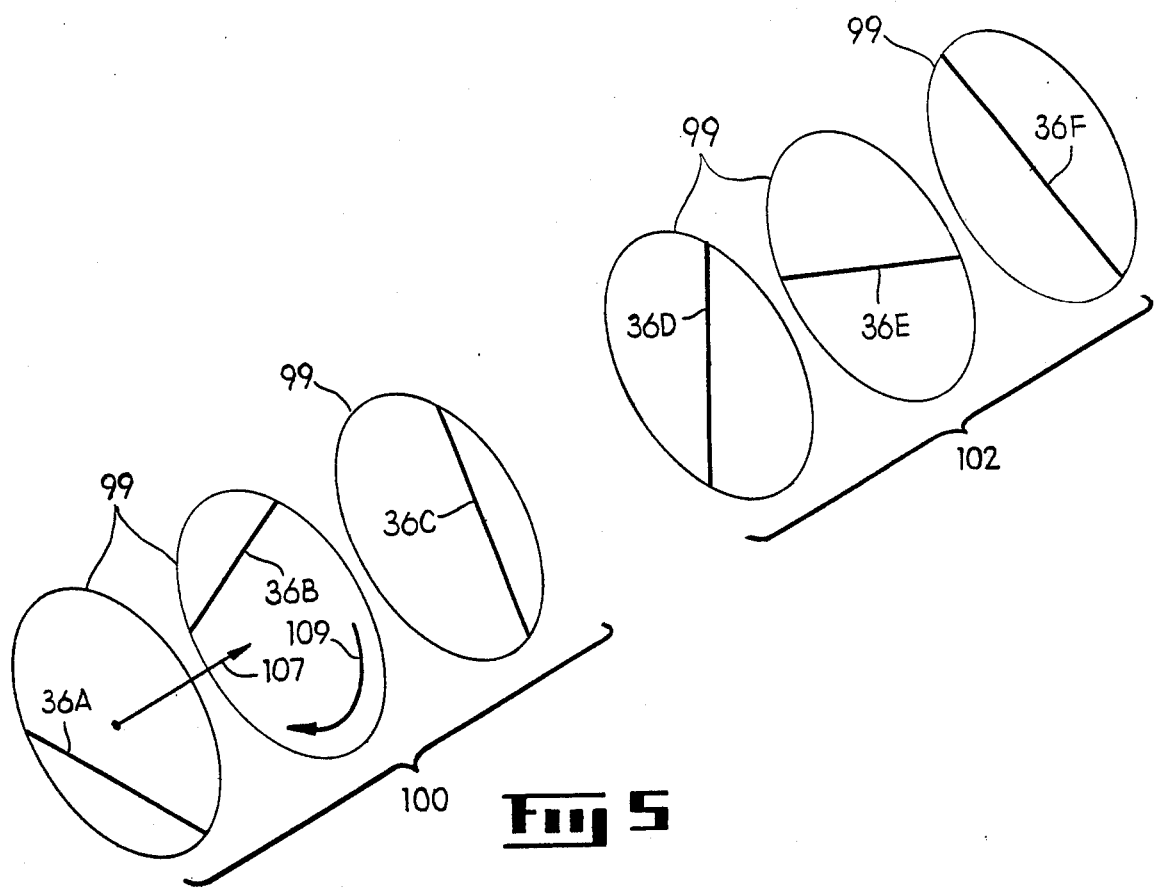
FIGS. 5 and 6 depict one configuration of the coil 27 in FIG. 2.
Figure 6:
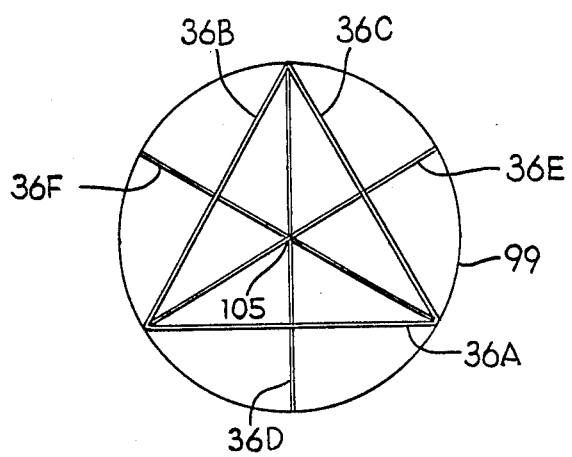

An inlet 3 (or inlet channel) for receiving a sample of an incoming airstream 6 is a cylindrical opening defined by the tip of a nose cone 9, which tapers down to thin edges 12. This tapering causes only a small disruption to the incoming airstream 6, thus allowing the airstream within the inlet 3 to maintain the pressure, temperature, and velocity characteristics of the incoming airstream 6.

The nose cone 9 is heated by heaters 15 (not shown in detail) to prevent ice formation, especially at the tip 18, which would disrupt or block incoming airstream 6. One such heater is Model No. SC121, 15 Watts, available from Hot Watt, Inc., located in Danvers, MA.

The inlet expands in diameter from point or station 21 to station 24, thus acting as a diffuser, which reduces the air velocity and very slightly increases the static pressure. However, incoming water droplets or ice particles (both will be referred to as "particulates") will have a higher inertia than the air itself, and will probably not slow as much. Speed reduction of particulates present in the airstream 6 is obtained by physical contact with a preheater 27 in an enlarged preheating channel 28. The preheater 27 contains a Cal-Rod coil which is wound in the shape of a conical helix, the apex being at point 30. Cal-Rod is a trademark of ARI Industries, located in Addison, IL. Cal-Rod herein refers to a resistance heating rod composed of Nichrome wires separated by MgO insulation and housed in a stainless steel sheath and, in this case, having a diameter of 0.040 in.

The configuration of the preheating coil 27 is such that no particulates in the incoming airstream see a clear path to the apex 30. FIG. 2 shows a view, in grossly exaggerated form, of apex 30 seen by the incoming airstream 6. The preheating coil 27 obstructs most direct paths between the inlet 3 and the apex 30. Consequently, entering particulates strike the preheating coil 27, or are diverted as shown by arrows 33 in FIG. 1 by the turbulence on the air which is caused by the coil. The preheating coil 27, together with the enlarged diameter in the preheating channel 28, serve to slow down both the incoming airstream and particulates.

The helical shape of the preheating coil 27 serves to induce a swirl into the mixture which enhances mixing of the water/gas mixture, which promotes homogeneity, thus making the dew point measurement more accurate. The Inventors point out that the spaces between the coil allow gas to flow through them, and present no significant blockage to gas flow.

A primary heating coil 36 in the schematic square wave configuration shown, further heats the now-slowed airstream as the airstream travels downstream to a collection tube 39. Under a diameter of inlet 3 of 3/16 inch, with an incoming airstream speed of 100 feet per second, with a maximum particulate concentration of 40 gm water per $m^3$ air, with a heat dissipation of 30 watts in the preheating coil and 1600 watts in the primary heating coil, all water or ice is vaporized by the time it reaches point 41, which is at the mouth of the collection tube 39. Downstream of the collection tube 39, the channel tapers in nozzle 43 which exhausts in channel 45.

The collection tube 39 ducts the vapor/air mixture to a dew point meter (or hygrometer) 40 which indicates the water content of the air at the collection tube inlet, at point 41.

In order for the reading from the dew point meter to be meaningful, the airstream ingested by the inlet 3 at point 21, must be of the same composition as that at point 44 in the incoming airstream 6. This condition is satisfied if the incoming airstream 6 is maintained in a state called isokinetic in the inlet 3. Isokinetic means that all molecules, whether they be air, or water in the form of vapor, droplets, or ice, maintain their same velocity (i.e., the same kinetic energy) in traveling from point 44 to point 21. An extreme example of the absence of the isokinetic state would be illustrated by partially plugging the downstream channel 45. With such plugging, the incoming airstream 6 will be drastically slowed or stopped, but water particles entering the intake will not be slowed so greatly: some water particles will continue to enter.

In order to assure that the flow is isokinetic at the inlet 3, one adjusts the flow through the collection tube 39. This adjustment can be done by altering the speed of a pump 47 (which draws gases through the collection tube 39 and supplies it to the hygrometer 40) adjusting a valve 49, or by other means. Irrespective of the particular adjustment means used, details of adjustment will be explained with reference to FIGS. 3 and 4.

FIG. 3 is a generalized plot of sampling accuracy versus orifice velocity which is widely assumed to be correct in the particulate sampling art. Orifice velocity refers to the airstream velocity at the intake 3 in FIG. 1. Sampling accuracy refers to the correspondence of the particulate concentration at point 44 in FIG. 1 to the concentration at point 21. For example, if there are ten particles per cubic centimeter at point 44, but only nine at point 21, the accuracy is 90 percent.

The inventors point out that, for a given range 52 of inlet velocities, the sampling accuracy is, to a large extent, independent of velocity. For example, if the velocity changes from about 95 to 100 in FIG. 3, in moving from point 53 to point 56, the sampling accuracy only changes from about 98 to 100. This feature can be used to modulate the airflow in the collection pipe 39 by application of FIG. 4.

FIG. 4 is a plot of dew point temperature as a function of the flow rate through the collection tube 39 (and thus through a part of the intake 3 at steady-state) in FIG. 1. Region 58 corresponds to region 52 in FIG. 3, as will now be explained.

If operation is in region 52 in FIG. 3, then sampling accuracy is high. If the water content of the incoming airstream 6 is not changing, as is the case in steady-state, then changes in the dew point of the airstream in the collection tube 39 will result from deviations in water content within the collection tube 39 from that in the incoming airstream 6. Changes in sampling accuracy cause this deviation. But, since the changes in sampling accuracy are small in region 52, then the changes in measured dew point will be small.

Therefore, one adjusts the flow within the collection tube 39 until one finds the region 58 in FIG. 4 where the dew point change is least for a given flow change. One finds the region of least slope on the dew point/hygrometer tube flow plot.

Another way to view the adjustment which uses FIG. 4 is the following. In the regions to the left of point 61, flow rate in the collection tube 39 is low. The low flow rate can be viewed as being caused by a flow restriction in the downstream channel 45 in FIG. 1. Flow of gases into the inlet 3 is thus reduced, but the momentum of particulates will cause them nevertheless to enter the inlet 3 and be vaporized by heating coils 27 and 36. The mixture collected by the collection tube 39 becomes "rich," as it were, because water content is artificially high as compared with that in the incoming airstream 6. The dew point of a rich mixture is high as shown in FIG. 4.

On the other hand, when flow rate is high in the collection tube 39, in the region to the right of point 64 in FIG. 4, the action of the pump 47 can be viewed as causing an increase in air speed within the inlet 3. This causes the gases in the incoming airstream 6 to accelerate faster than the particulates in the inlet, with the result that particulate concentration in the inlet 3 goes down, and the mixture collected by the collection tube 39 becomes "lean." A lean mixture has a lower dew point, as shown in FIG. 4.

However, when the hygrometer flow rate is within range 58, the small change 67 of the dew point in jumping from point 61 to 64 indicates that the particulate content within the inlet 3 in FIG. 1 is approximately the same as that at point 44. The small change 67 in dew point with flow rate indicates that the orifice velocity is within the range 52 in FIG. 3, because that is the region where sampling accuracy changes little with changes in flow rate.

The preceding discussion has considered flow properties of the invention. This discussion will now turn to structural features. Cylindrical insulating sleeves 70 and 72 are constructed of Macor. Macor is a trademark of the Corning Glass Works, located in Corning, N.Y., and is used herein to refer generally to a machinable ceramic. Macor is a good electrical insulator at high temperature, but a poor thermal insulator. An air space 75 lies between the insulating sleeves 70 and 72 and an outer cylinder 77 which is preferably a stainless steel. Machined rings 80 support the insulating cylinders 70 and 72 and maintain the air space 75. The insulating air space 75 reduces heat loss from the coils 27 and 36 to the exterior. This reduction is important because the invention is intended to be used in freezing conditions, under a spray of freezing water and ice.

As stated above, downstream of the collection tube 39 is a nozzle 43 followed by a diffuser 45. These function as follows.

The inlet 3 and the diffuser 45 have external surfaces 3A and 45A which are tapered, thereby providing reduced disruption to the external airflow.

Representative diameters of the channel diameter at the stations identified in FIG. 1 are given in Table 1.

TABLE 1

| Station | Diameter |
|---|---|
| 21 | 3/16 inch |
| 24 | ¼ |
| 80 | 9/32 |
| 80A | ⅜ |
| 84 | ⅜ |
| 87 | 5/16 |
| 89 | ¼ |
| 92 | ¼ |

The preceding discussion has described primary heating coil 36 as having a square wave shape for ease of explanation. However, in one form of the invention, the shape is that shown in FIG. 5. The circles 99 in FIG. 5 represent the cylindrical channel within the insulating sleeve 72. The heating coil 36 is divided into an upstream region 100 and a downstream region 102. In the upstream region 100, the heater wires lie on chords 36A–C of circles 99, the circles 99 being cross sections of the cylinder where the wires lie. Accordingly, the upstream wires 36A–C, when viewed together, appear as a triangle when seen from arrow 6 in FIG. 1, as shown in FIG. 6.

In the downstream region 102, the heater wires 36D-F lie on diameters of circles 99. The downstream wires again, when viewed together, appear as a starburst in FIG. 6 when viewed from arrow 6 in FIG. 1. This triangular-starburst wire configuration produces at least three results.

One, the upstream wires 36A–C tend to heat the walls of the insulating sleeve 72 in FIG. 5, while the downstream wires 36D-F tend to heat the air in the center 105 in FIG. 6 of the channel. Two, spacing out the wires 36A–F in circles 99 reduces drag as compared with an alternative, namely, placing all wires arranged to support the swirl introduced by the helical preheating coil 27. That is, if the swirl is clockwise when seen from arrow 6 in FIG. 1, then the upstream wires are also clockwise: when seen from arrow 6 in FIG. 1, a downstream wire 36B is positioned clockwise with respect to an upstream wire 36A.

In more complex terms, the swirling flow can be ascribed axial component 107 and circumferential component 109 in FIG. 5. As to the wires, when one travels axially, in the direction of component 107, from an upstream wire 36A to a downstream wire 36B, one must also have a circumferential component 109 in order to reach the downstream wire 36B.

An invention has been described for isokinetic collection and evaporation of particulate water in an airstream moving at, say, 100 feet per second. An inlet channel expands into a larger cross section, thereby reducing the air speed, thus reducing internal drag. The drag reduction is important because drag acts as a partial blockage of the inlet 3, thus rendering the inlet flow nonisokinetic with respect to the incoming airstream, as explained above. The speed reduction also increases the dwell time of the water/gas mixture within the probe, thus giving the heaters 27 and 36 more time to heat the gas. With a probe length (i.e., the distance between stations 21 and 92) of 22 inches, and with an air speed of 100 ft/sec, it takes about 0.183 seconds for the air mixture to travel externally from station 21 to station 92. The internal air takes about 0.524 seconds. A preheating coil 27 acts as an obstruction, causing incoming particulates to strike the coil, perhaps break up, and reduce in speed. A primary heating coil 36, of smaller diameter wire than the preheating coil 27 because it need not withstand the buffeting of incoming particulates, vaporizes the water particulates. The vaporized mixture, which has increased in speed somewhat because of the expansion due to the vaporization, is collected by a collection pipe 39 and transmitted to a hygrometer 40. The invention adjusts the flow in the collection pipe 39 in order to maintain the inlet in the isokinetic state.

Numerous substitutions and modifications can be undertaken without departing from the true spirit and scope of the present invention.

What is desired to be secured by Letters Patent is the invention defined in the following claims.

1. In a system for measuring the liquid water, water vapor and ice content of a moving airstream under icing conditions, the improvement, comprising:
    (a) inlet means for collecting a sample of the airstream; and
    (b) means for maintaining the sample in a substantially isokinetic state with respect to the moving airstream, said means including a dew point measuring means for measuring the dew point of the sample, and adjustment means for adjusting flow through the inlet means in order to alter the dew point of the sample.

2. A system for measuring the liquid water, water vapor and ice, content of a moving gas stream under icing conditions, comprising:
    (a) means for receiving a sample of the gas stream at an inlet;
    (b) means for vaporizing liquid and ice in the sample;
    (c) means for measuring water content of the sample of (b); and
    (d) means for causing the water content of the sample to be similar to the water content of the gas stream by setting velocity of the sample such that rate of change of dew point of the sample with respect to velocity of the sample is near minimal.

3. A system for measuring the water content, in vapor, liquid, and solid states, of a moving airstream under icing conditions, comprising:
    (a) an inlet for admitting a sample of the moving airstream;
    (b) a diffusing channel downstream of the inlet for reducing the speed of the sampled air;
    (c) heating means contained in the diffusing channel for
        (i) heating the sampled air and
        (ii) obstructing the flow of particulates in the sampled air;
    (d) second heating means located downstream of the first heating means for further heating the sampled air and for vaporizing water contained in the sampled air;
    (e) a collection tube located downstream of the second heating means for collecting some of the vaporized water/air mixture;
    (f) flow regulation means for adjusting the flow rate of the collected water/air mixture in paragraph (e) to allow the sampled air in the inlet of (a) to be substantially isokinetic with the moving airstream; and
    (g) means for measuring the water content in the collection tube.

4. A system for measuring the water content of a moving airstream which contains water in the vapor, liquid, and solid states, comprising:
    (a) a nose cone (i) having an inlet channel for receiving a sample of the airstream and (ii) lacking moving parts upon which water may collect and freeze;
    (b) a first heater for heating the nose cone in order to prevent ice from blocking the inlet channel;
    (c) a preheating channel of larger cross-sectional area than the inlet channel, for receiving the sample from the inlet channel;
    (d) a preheating coil located in the preheating channel and having a shape resembling a conical helix for inducing swirl into the sample;
    (e) a circular collection channel for receiving the sample from the preheating channel, and having substantially the same cross-sectional area as the preheating channel;
    (f) a primary heater located in the circular collection channel and comprising two sections, namely,
        (i) an upstream section in which the heater includes an array of wires lying on chords of the circular collection channel;
        (ii) a downstream section in which the heater includes an array of wires lying approximately on diameters of the circular collection channel;
    (g) a collections means for withdrawing air-vapor mixture from the circular collection channel; and
    (h) means for adjusting the rate of withdrawal of the collection means in response to the dew point of the withdrawn air-vapor mixture.

* * * * *